United States Patent [19]

DeCote, Jr. et al.

[11] Patent Number: 4,640,285
[45] Date of Patent: Feb. 3, 1987

[54] SENSE MARGIN EVALUATION SYSTEM AND METHOD FOR USE SAME

[75] Inventors: Robert DeCote, Jr., Miami Beach; Peter P. Tarjan, Miami, both of Fla.

[73] Assignee: Cordis Corporation, Miami, Fla.

[21] Appl. No.: 693,675

[22] Filed: Jan. 22, 1985

[51] Int. Cl.$^4$ ............................................. A61N 1/36
[52] U.S. Cl. ....................................... 128/419 PT
[58] Field of Search ............. 128/697, 419 PT, 419 P, 128/419 PG

[56] References Cited

U.S. PATENT DOCUMENTS

| | | | |
|---|---|---|---|
| 3,508,538 | 4/1970 | Keller, Jr. | 128/419 PT |
| 3,625,201 | 12/1971 | Murphy, Jr. | 128/419 PT |
| 3,718,909 | 2/1973 | Greatbatch | 128/419 PT |
| 3,757,790 | 9/1973 | Herrmann | 128/419 P |
| 3,769,986 | 11/1973 | Herrmann | 128/419 PT |
| 3,777,762 | 12/1973 | Nielsen | 128/419 P |
| 3,800,801 | 4/1974 | Gaillard | 128/419 P |
| 4,102,346 | 7/1978 | Fulker | 128/419 PT |
| 4,142,533 | 3/1979 | Brownlee et al. | 128/419 PT |
| 4,245,643 | 1/1981 | Benzing, III et al. | 128/419 PT |
| 4,290,430 | 9/1981 | Bihn et al. | 128/419 PT |
| 4,295,468 | 10/1981 | Bartelt | 128/419 PT |
| 4,337,776 | 7/1982 | Daly et al. | 128/419 PT |
| 4,476,869 | 10/1984 | Bihn | 128/419 PT |

*Primary Examiner*—William E. Kamm
*Assistant Examiner*—Mitchell J. Schein
*Attorney, Agent, or Firm*—Henry W. Collins; Thomas R. Vigil

[57] ABSTRACT

The sense margin evaluation system and method for use of same is based upon (1) the interposition of a variable broad-band attenuator between an implanted cardiac pacer lead set and a pacer which is about to be implanted and (2) the inclusion of a pacer pulse detector at the pacer port. In use, the pacer is first programmed to a standby mode and a condition of 100% inhibition with the attenuator set to 0 dB. This affirms that the pacer's sense amplifier can sense the cardiac signal. Then, attenuation is incrementally added until the pacer just begins to output. The attenuation ratio (input/output) at this point is a direct measure of the ratio effective between the patient's cardiac signal and the pacer's sensing threshold, i.e., the sense margin. The advantage of this technique is that by using a broad-band attenuator, measurement inaccuracies due to the convolution of the cardiac signal's spectral content with a pacer system analyzer and a pacer sense amplifier's disparate narrow-band frequency response are avoided. The patient's cardiac signal serves as the test waveform generator for the pacer that is about to be implanted in his body and the sense amplifier'frequency response is identically that of the pacer about to be implanted.

36 Claims, 6 Drawing Figures

SENSE MARGIN EVALUATION SYSTEM AND METHOD FOR USE SAME

BACKGROUND OF THE INVENTION

1. Field of the Invention

The present invention relates generally to a method and apparatus for matching a pacer to a patient's heart, and more particularly to a method and apparatus for matching the sensitivity threshold of a pacer's sense amplifier with the effective cardiac signal strength of a patient's heart. The system and method are particularly well adapted for use in a pacer system analyzer, wherein the operation of a pacer is monitored in association with a patient's heart prior to implantation.

2. Description of the Prior Art

To assist physicians in treating cardiac disorders of the type for which the use of implantable cardiac pacers is indicated, pacer system analyzers (PSA's) have been developed. These devices are used at the time of pacer implantation to efficiently measure the parameters of a pacer system, including a patient's heart, a pacer and implanted pacer leads, without the need to perform separate procedures requiring multiple interconnections and an undesirably long time to complete. Pacers to be implanted are tested for proper programming and operation, not only while connected in a simulated pacing system environment, but also while operating in the actual system in which they are to be used. Moreover pacer system analyzers are preferably equipped to generate pacing pulses as required to support the patient during the pacer implantation process, independently of the pacer to be implanted.

By using a pacer system analyzer, a physician is able to adjust the operating parameters of a pacer system as required to suit the specific needs of an individual patient before the pacer has been fully implanted and the implantation surgery completed. This minimizes the need for inconvenient and potentially injurious post-implantation adjustment of the pacer or its associated pacer leads.

One important parameter of a pacer system is the sensing margin of the pacer to cardiac activity as sensed by the pacer leads. It is desirable that the pacer be sufficiently sensitive to reliably recognize and respond to the activity of the heart, but not so sensitive as to respond to extraneous noise or motion artifacts inherently present in the pacer lead system.

In prior pacer system analyzer constructions the peak or other voltage level of the cardiac pulse as sensed at the cardiac pacer lead was first measured, and the sensitivity of the pacer was then set so that the pacer responded to signals of that voltage level. Unfortunately, this did not always provide reliable sensing because of differing frequency spectrum characteristics of the pacer, the PSA, and the cardiac signal. Consequently, the physician was forced to either set the sensitivity of the pacer undesirably high, thereby risking response to noise and motion artifacts, or to set the pacer sensitivity at the cardiac signal level, thereby risking having to post-operatively alter the placement of the pacer lead or adjust pacer sensitivity in the event of inadequate cardiac signal. The present invention is directed to a measurement system and method for use in a pacer system analyzer which avoids this problem through pre-implantation use of a novel user-controllable broadband attenuator element between an operatively connected cardiac lead and a pacer to establish a true sensing margin for the implanted pacer and lead combination.

In operation, in previous pacer system analyzers the terminals of an implanted pacer lead were first connected to a surrogate sensing amplifier within the analyzer. This sensing amplifier had a predetermined sensitivity calibration with a specific test signal and a predetermined frequency response, which was designed for a "typical heart" and which was considered a "standard". Then, with the analyzer, the physician determined the level of signal picked up from the patient's heart and matched it with a pacer having a somewhat higher bench tested sensitivity.

However, the sensing amplifier in the pacer did not necessarily have the same calibration as the surrogate sensing amplifier in the PSA, and more particularly, did not necessarily have the same frequency response characteristics. As a result, the pacer, when connected to the patient's heart, did not necessarily have the same effective sensitivity as the surrogate test sensing amplifier. Accordingly, the pacer connected to the patient's heart was not necessarily able to sense low level cardiac signals from the patient's heart, or worse yet, would marginally sense the patient's heart signal.

Heretofore various devices have been proposed for matching a pacer to a patient's heart and examples of such previously proposed devices are disclosed in the following U.S. patents:

| U.S. Pat. No. | PATENTEE |
| --- | --- |
| 3,757,790 | Herrmann |
| 3,777,762 | Nielsen |
| 3,800,801 | Gaillard |
| 4,245,643 | Benzing, III et al |
| 4,290,430 | Bihn et al |
| 4,337,776 | Daly et al |

The Hermann U.S. Pat. No. 3,757,790 is directed to a capture threshold analyzer and stimulating testing device with an internal generator. The circuitry used is complicated and the device does not appear to be adapted for in vivo cardiac signal sensing analysis.

The Nielsen U.S. Pat. No. 3,777,762 discloses only a pacemaker output control circuit.

The Gaillard U.S. Pat. No. 3,800,801 is directed to a heart stimulation apparatus and method of testing its installation including means for attenuating the pacing and separate means for picking up calibrated pulses and displaying same.

The Benzing, III, et al. U.S. Pat. No. 4,245,643 discloses an apparatus for measuring contact resistance of a pacing electrode.

The Bihn, et al. U.S. Pat. No. 4,290,430 is directed to a pacer analyzer wherein an analog signal is converted to a digital signal and then back to an analog signal. The pacer is not connected directly to the heart in this analyzer. Rather, pulses from the heart are digitized, stored and then analog conversion thereof is applied to the pacer.

Although the circuitry disclosed in the Bihn, et al. patent attempts to achieve a function similar to the function of the sense margin evaluator of the present invention, it does so in a different and more complicated fashion. In this respect, the sense margin evaluation system of the present invention utilizes in-vivo real time evaluation of a heart signal. In contrast, the circuitry disclosed in the Bihn, et al. patent uses a microprocessor system to do an A/D conversion followed by storage and subsequent D/A playback with a scaling factor injected into the procedure.

The Daly, et al. U.S. Pat. No. 4,337,776 is directed to an impedance measuring pacer which facilitates measurement of both electrode impedance and stimulation threshold.

As will be described in greater detail hereinafter, instead of comparing the sensitivity of the pacer sense amplifier with a "test" standard and measuring sensitivity, which is frequency dependent and which can vary for different sensing amplifiers in different pacers and in different PSA sensing amplifiers because of different frequency response characteristics, the sense margin evaluation system of the present invention provides for coupling of the implanted cardiac lead of a cardiac pacing system to a broad-band variable attenuator having its output connected to the system pacer, so that a meaningful matching of a particular pacer to a particular heart is obtained.

With the sense margin evaluation system of the present invention, instead of specifying different levels of sensivity in millivolts with respect to a test signal, the ratio, or "sense margin", of effective cardiac signal strength relative to the actual sensing amplifier threshold is measured and specified. This ratio will preferably be between 2:1 and 5:1 and can, for example, be 4:1.

SUMMARY OF THE INVENTION

According to the invention, there is provided a system for determining the ratio or "sense margin" of the strength of a cardiac signal (R-wave or P-wave) from a patient's heart relative to the minimum amplitude sensed by a pacer's sense amplifier where:

$$\text{Sense Margin} = \frac{\text{Effective cardiac signal strength}}{\text{Effective pacer sense amplifier threshold}}$$

The system comprises an adjustable broad-band attenuator circuit having an input and an output; first means for coupling the attenuator circuit input to at least one cardiac lead connected to a patient's heart; and second means for coupling the attenuator circuit output to the sense amplifier of a pacer to be implanted. A pulse detector is also coupled to the attenuator circuit output.

Further according to the invention there is provided a method for determining the ratio or "sense margin" of the strength of a cardiac signal (R-wave or p-wave) from a patient's heart to the minimum amplitude sensed by a pacer sense amplifier in a pacer to be implanted where:

$$\text{Sense Margin} = \frac{\text{Effective cardiac signal strength}}{\text{Effective pacer sense amplifier threshold}}$$

The method comprises at least the steps of: coupling a sensing/pacing cardiac electrode to a patient's heart; coupling a lead from the cardiac electrode to a broadband attenuator circuit; coupling the output from the broad-band attenuator circuit to a pacer sense amplifier in a pacer; coupling a pacing pulse detecting circuit to the attenuator/pacer interface; attenuating the cardiac signals received while simultaneously monitoring the output of the pulse detecting circuit to determine if a pacer pulse has been issued; noting when a pacer pulse is detected and the amount of attenuation; converting the amount of attenuation to a ratio; determining if the ratio or sense margin is acceptable, and if so, proceeding with the implanting of the pacer, and if not, taking corrective action such as checking the electrode connection to the heart and the pacer circuitry and/or adjusting the gain of the sense amplifier, or repeating the above steps with a new cardiac electrode coupled to the heart and/or a new pacer.

In order to properly use the sense margin evaluation system, a set of initial conditions must first be established, as follows:

(1) the attenuator circuit must, in general, be adjusted to 0 dB;

(2) the pacer must be programmed to a "standby" mode, i.e., either AAI or VVI, as appropriate;

(3) the pacing rate of the pacer to be implanted must be set lower than the patient's lowest intrinsic rate; and (4) the pacer's sensing threshold must be set below the effective cardiac signal level, i.e., it must sense the cardiac signal.

Under these conditions, the pacer will be 100% inhibited; assuming a properly functioning pacer. The user confirms this initial condition by observing that the pace indicator of the PSA does not illuminate.

Given the "100% inhibited, 0 dB" initial condition just defined, the user next inserts the minimum amount of attenuation that will cause the pacer to start pacing. This new condition will activate the pulse detector and become apparent to the user as periodic flashes of light from the appropriate PSA pace indicator.

By way of illustration, if the attenuator requires 6.0 dB to initiate pacing, the amplitude of the cardiac signal entering the attenuator is exactly twice that of the sense amplifier's threshold. Therefore the sense margin in this example would be 2.0:1.

According to the teachings of the present invention, this ratio is the parameter of real interest to the user. Because the attenuator is broad-band, neither the frequency response of the pacer's sense amplifier, nor that of the PSA's sense amplifer (which is not used), nor the spectral content of the cardiac signal, affects the ratio measurement.

DESCRIPTION OF THE PREFERRED EMBODIMENT

Figure 1:
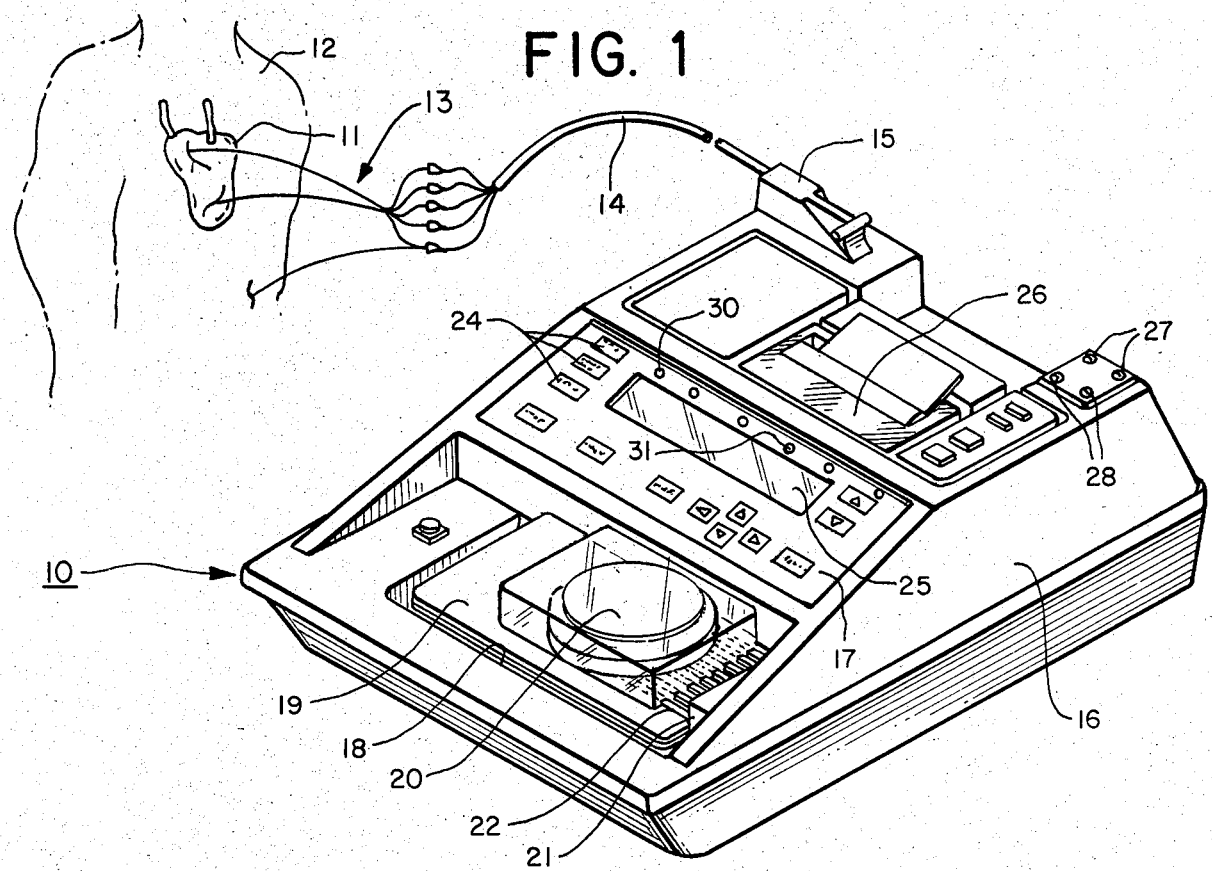
FIG. 1 is a perspective view of a pacer system analyzer incorporating a sense margin evaluation system constructed in accordance with the teachings of the present invention.

Referring now to the Figures, and particularly to FIG. 1, a pacer system analyzer (PSA) 10 is shown which incorporates a sense margin evaluation system constructed in accordance with the teachings of the present invention. As illustrated, the PSA 10 is connected to the heart 11 of a patient 12 by means of a pacer lead set 13, which may be conventional in construction and operation. The pacer lead set 13 is electrically connected to the PSA 10 by means of a twelve (12) foot long PSA cable 14 having alligator clips at the distal end thereof and a multicontact connector 15 at the proximal end thereof connected to the PSA 10.

The PSA 10 is contained within a generally rectangular housing 16 formed of a durable, insulating plastic or like material and includes a sloping, generally flat, control panel 17. A portion of the housing 16 is formed to provide a receptacle 18 for receiving a sealed package 19 containing a sterile implantable cardiac pacer 20. A connector 21 in receptacle 18 engages a plurality of electrical contacts 22 formed on package 19 to provide electrical communication between the PSA 10 and the pacer 20. This is called a pace-thru package and is described in more detail in U.S. Pat. No. 4,423,732. In the absence of a so-called pace-thru package 19, an interface cable/connector (not shown) is to be used between the pacer 20 and the PSA connector 21.

Panel 17 includes a plurality of pressure sensitive user-actuated push button controls 24 and a liquid crystal display (LCD) 25. PSA 10 operates in one of several user-selected modes in accordance with entered key stroke commands. To assist the user in selecting the appropriate operating mode, a series of internally generated instructions and a plurality of measured pacer system operating parameters are displayed on LCD 25. A printer mechanism 26 provides a printed record of measured pacer system operating parameters and measured patient parameters, and two pairs of ICEG electrodes 27 and 28 provide isolated atrial and ventricular cardiac signals for connection to external instrumentation.

To provide an indication of pacer operation, the PSA 10 further includes, in accordance with the teachings of the present invention, atrial and ventricular pacing lights 30 and 31, along the top edge of control panel 17.

The patient's heart 11 is connected via pacer lead set 13 and the alligator clips on PSA cable 14, connector 15 and PSA 10 to the pacer 20 to form a pacer system. PSA 10 functions to automatically measure various parameters of this pacer system thereby to assist a physician in selecting, implanting and adjusting the pacer system components for maximum effectiveness. Additionally, proper operation of the pacer system can be verified before final implantation, and pacing pulses for supporting the patient during pacer system implantation can be generated.

Figure 2:
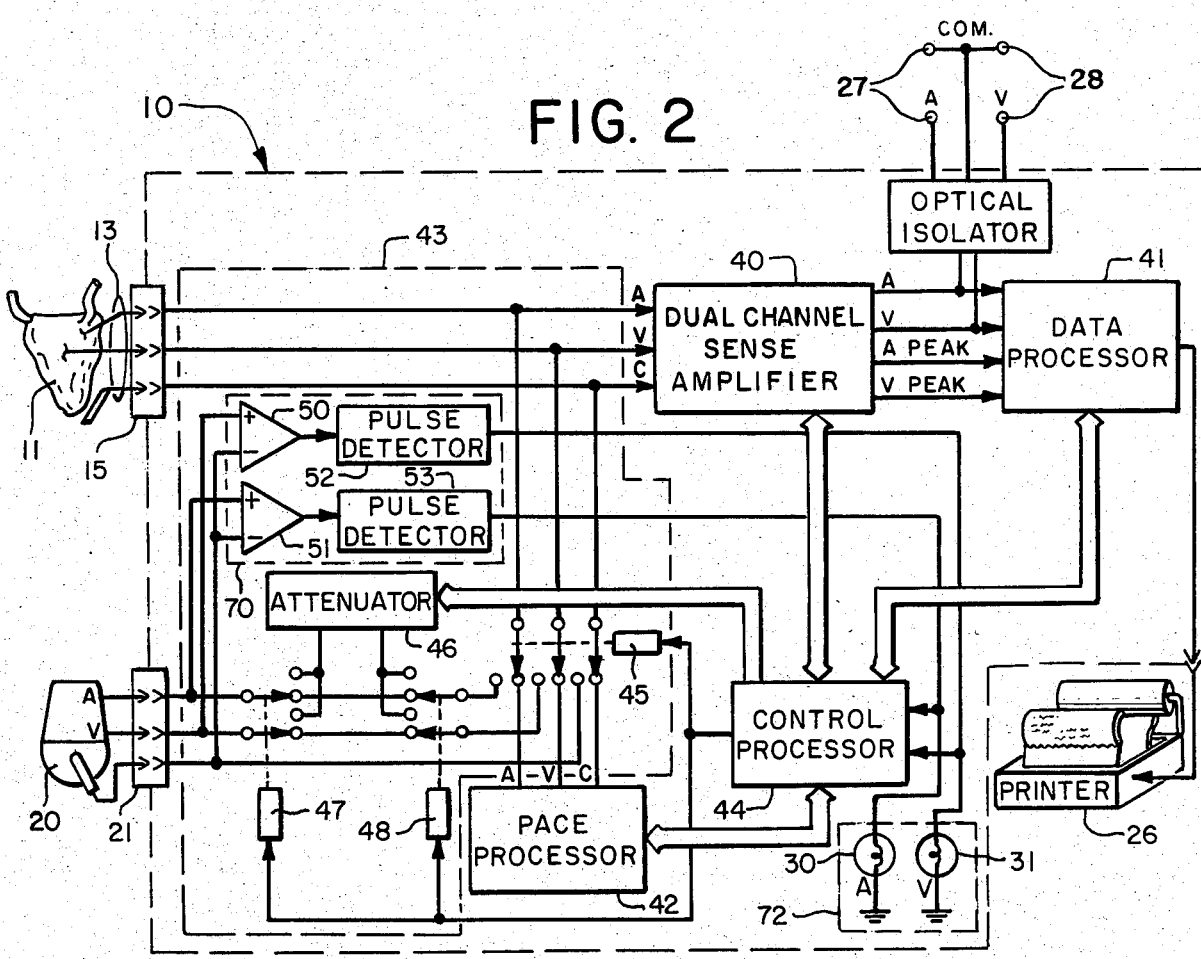
FIG. 2 is a simplified functional block diagram of the pacer system analyzer of FIG. 1.

Referring to the simplified PSA system functional block diagram of FIG. 2, PSA 10 includes a dual channel sense amplifier 40 for amplifying sensed cardiac signals, a data processor 41 for processing the sensed signals, a pace processor 42 for generating atrial and/or ventricular pacing signals, an interface circuit 43 for coupling the patient's heart 11 and implantable pacer 20 to the pacer system analyzer, and a control processor 44 for controlling the operation of the analyzer components. Control processor 44 is preferably microprocessor based and is programmed to generate system control voltages in response to user-entered keystroke commands from control panel 17 (FIG. 1). Additionally, the control processor 44 may generate a series of user instructions for display on LCD 25.

To facilitate measurement of patient parameters and to provide basic patient life support, pace processor 42 generates pacing pulses for application to the heart 11. Atrial and ventricular pacing pulses of predetermined amplitude, duration and rate are generated in the pace processor 42 in accordance with applied pace control signals from control processor 44. The pacing pulses are outputted from the pace processor 42 through interface 43 for application to the heart 11 through the connections of connector 15, the PSA cable 14 and the alligator clips to the cardiac pacer lead set 13.

As further illustrated in FIG. 2, the pacer 20 is connected by connector 21 to interface circuit 43. Upon application of an appropriate control signal from control processor 44, interface circuit 43 couples cardiac lead set 13 to pacer 20 through a relay 45 whereupon the heart 11 is paced by the pacer 20. Accordingly, by producing appropriate control signals, the control processor 44 can cause the heart to be paced by either pace processor 42 or by implantable pacer 20.

Atrial and/or ventricular intracardiac signals detected by the cardiac pacer lead 13 are applied to respective inputs of sense amplifier 40 via the alligator clips, PSA cable 14, connector 15 and the PSA 10. The sense amplifier 40 generates atrial and/or ventricular strobe signals for application to control processor 44 upon the occurrence of atrial or ventricular intracardiac signals above a predetermined threshold. Additionally, the sense amplifier provides amplified atrial and ventricular signals for application to data processor 41 and for application to IECG terminals 27 and 28 through an isolation circuit, as well as signals indicative of peak atrial and ventricular R-waves sensed by cardiac lead set 13. Data processor 41 performs the mathematical operations required to calculate various patient or pacer system operating parameters for display on LCD 25 or for printing by printer 26.

Within interface circuit 43, PSA 10 includes, in accordance with the teachings of the present invention, a broad-band programmable attenuator 46 which may be selectively switched into and out of series-circuit relationship with pacer 20 by means of a pair of relays 47 and 48. A pair of amplifiers 50 and 51, in conjunction with respective pulse detector circuits 52 and 53, provide signals indicative of operation of pacer 20 to control processor 44 and atrial and ventricular pace indicators 30 and 31.

Figure 3:
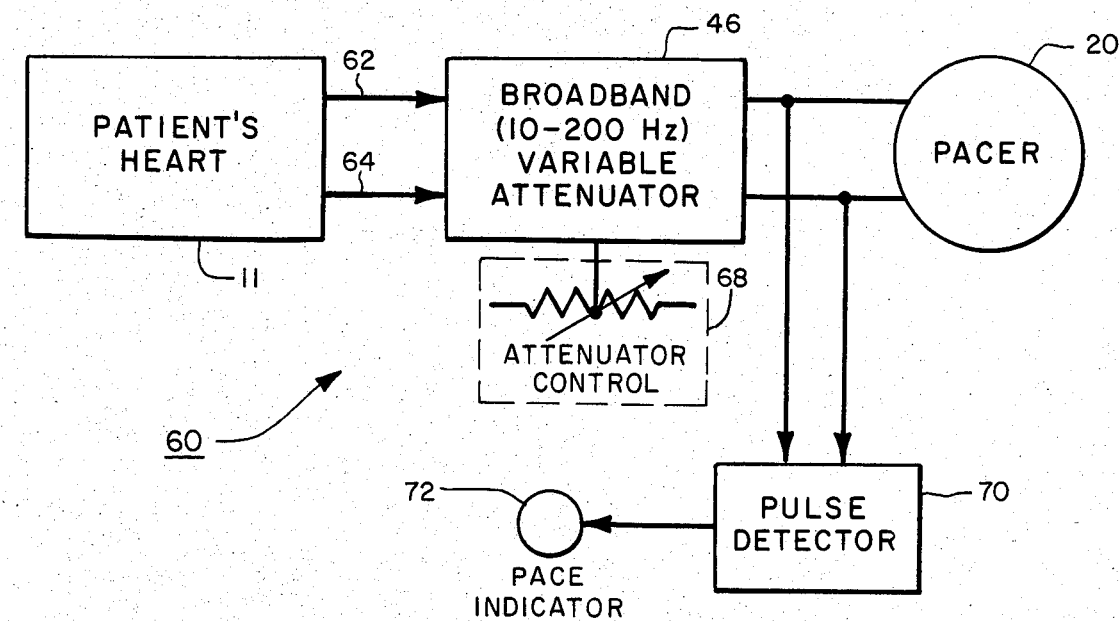
FIG. 3 is a simplified functional block diagram of the sense margin evaluation system of the present invention.

Referring to FIG. 3, a sense margin evaluation system constructed according to the teachings of the present invention may be generally identified by reference numeral 60. The evaluation system 60 includes connection or coupling means 62, 64 for establishing electrical connection with the patient's heart 11. Typically this is achieved by anchoring a conventional epicardial or endocardial lead, such as the cardiac pacer lead set 13, with an electrode assembly at the distal and of the lead set 13 in contact with the heart 11 and connecting same with PSA cable 14 to the PSA 10.

The cardiac signal picked up by the sensing electrode or electrodes is sent to variable attenuator 46, which is preferably sufficiently broad-band to convey signals over at least a 10 to 200 Hz range. Attenuator control means, generally indicated as 68 in FIG. 3, is coupled to the broad-band variable attenuator 46 for adjusting the attenuation thereof. The pacer/attenuator interface is connected to a pulse detector 70 and pace indicator 72, and to a pacer sense amplifier (not shown) within the pacer 20. These elements are shown as employed in a typical PSA embodiment in FIG. 2.

In using the sense margin evaluation system 60, the attenuation provided by attenuator 46 is gradually increased, starting, for example, from 0.0 dB and increasing toward 19.9 dB. After each 0.1 dB step change in attenuation obtained by manipulation of attenuator control 68, an operator or a physician will monitor pace indicator 72 to determine whether or not a pulse has been sensed. At the same time the attenuated cardiac signal, as attenuated by attenuator 46, is supplied to pacer 20.

The operator continues to increase the attenuation of the cardiac signal until the sense amplifier in pacer 20 fails to sense the attenuated cardiac signal, at which time the pacer begins to generate pulses which are picked up by the pulse detector 70 and displayed on pace indicator 72. When this occurs, the operator knows that the threshold of the pacer sense amplifier has been reached and the amount of attenuation can be read.

The attenuation can then be converted to a ratio referred to as the sense margin wherein:

$$\text{Sense Margin} = \frac{\text{Effective cardiac signal strength}}{\text{Effective pacer sense amplifier threshold}}$$

A safe margin is typically 4:1, but can be lower or higher, and can range in practice from 1.1:1 to 10:1, or higher.

Assuming that a desired minimum or target value ratio is 4:1, if the operator notes that the measured ratio is 3:1, several steps can be taken. First of all, if access can be gained to the pacer sense amplifier, the gain of the amplifier can be increased. If not, another pacer can be connected in place of pacer 20 and the above evaluation can be repeated. Alternatively, where the connection of the cardiac pacer lead electrode to the heart 11 is not adequate, the physican can check the lead electrode connection, and insert a new lead or reconnect the existing lead at a different position within the heart 11, and repeat the above steps to verify that a satisfactory sense margin is obtained.

With the sense margin evaluation system of the present invention, the patient's own heart signals are used as a test source, as opposed to an artificially created cardiac test signal. The evaluation system does not yield an absolute value for sensitivity, but rather a relative ratio of the particular cardiac signal to the particular sense threshold, defined herein as the sense margin. Essentially, the evaluation system temporarily interfaces a patient and pacer through an adjustable attenuator 46 to evaluate the sense margin, instead of comparing sensitivity requirements and measured values using "standard" test signals.

To insure that the sense margin evaluation system performs the desired function, a broad bandpass of at least 10 to 200 Hz is provided for the attenuator 46 so that any mismatch between the spectrum of the cardiac signal and the frequency response of the pacer sense amplifier will not be altered by the frequency response of the attenuator.

It will be appreciated that the functional block diagram shown in FIG. 3 is merely illustrative of the basic system and can be implemented in several ways. For example, the attenuator 46 can be replaced with a suitably connected digital-to-analog converter, a programmable gain amplifier, or analog signal multiplier. Further, the signal from the patient's heart 11 can be amplified, converted from analog to digital form, and then scaled digitally with subsequent digital-to-analog conversion as an in vivo attenuation technique. Furthermore, the pulse detector 70 may drive a meter, scope, loudspeaker, or microprocessor input, as opposed to the LED pace indicator 72.

The matching of a typical sense amplifier in a pacer 20 to a patient's heart 11 can be effected without incurring the misunderstandings that have frequently arisen in the past between physicians and pacemaker manufacturers. For example, a pacer with a bench tested sensitivity of 2.0 mV may fail to sense a patient's cardiac/heart signal which is known to contain peaks of 3 mV or greater due to a mismatch between the spectra of the heart signal and the calibration signal convoluted with the frequency response of the amplifier. Prior attempts at standardizing test signals have not resolved this spectral mismatch problem, nor will they, because the spectral content of each patient's cardiac signal differs.

The sense margin evaluation system of the present invention optimally solves the spectral mismatch problem by using the patient's own heart signal as a test source and by passing the patient's heart signal in an undistorted manner through the broad-band variable attenuator 46 to pacer 20. The output signal from attenuator 46 is in parallel with the high input impedance pulse detector 70 which monitors pacer 20.

In particular, if the pacer sensitivity is adequate, then pacer 20 output pulses will be inhibited at zero attenuation. The attenuation is slowly increased until output pulses begin to appear from the pacer. This condition indicates that the system is no longer sensing. Backing up slightly until the output pulses vanish again establishes the attenuator 46 setting at the measure of sense margin. For example, if the attenuator 46 is calibrated in decibels and it takes 20 decibels to provide marginal sensing at a given pacer sensivity, then the operator or physician knows that the "sense margin" is 10:1. This implies that the level of the sensed cardiac signal could be reduced to 1/10th of its original level, as by natural causes (such as fibrotic tissue buildup around the pacer lead tip), before being marginally sensed at that reduced level by the pacing sense amplifier. Alternatively, the sensitivity of the pacer sensing amplifier can be reduced before experiencing loss of sensing.

Figure 4:
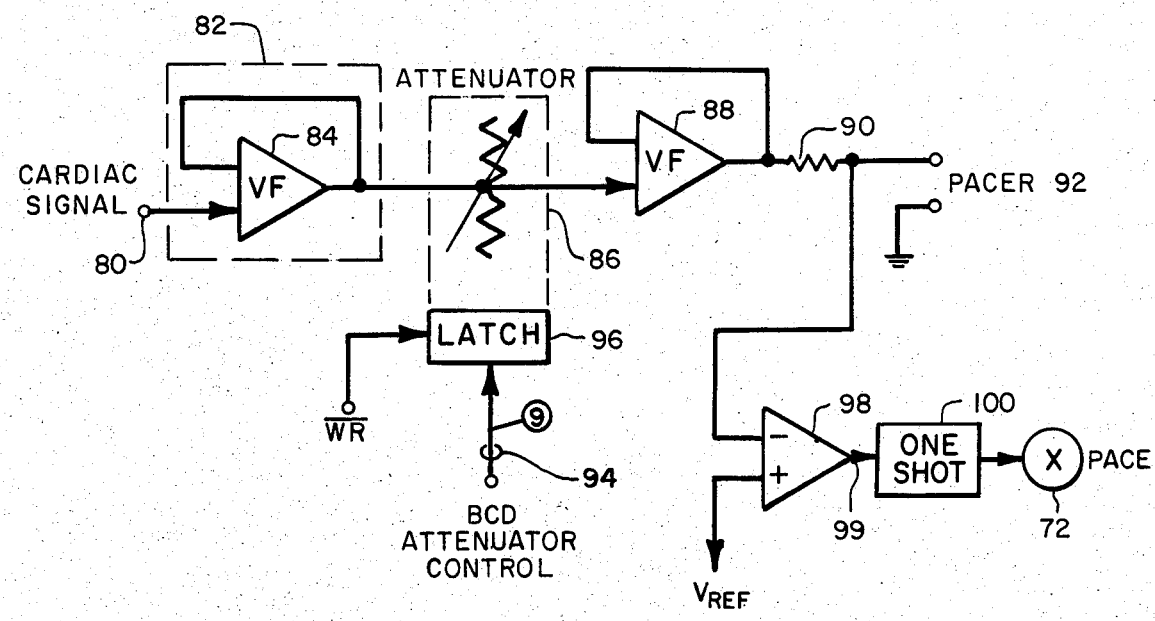
FIG. 4 is a more detailed functional block diagram of an embodiment of the sense margin evaluation system.

FIG. 4 illustrates more specifically a practical implementation of the sense margin evaluation system. Here the patient's heart signal is fed into an input 80 of a broad-band bandpass buffer amplifier circuit 82 which includes an operational amplifier 84. The output of the amplifier 82 is fed to an attenuator 86 which can, for example, be a programmable step attenuator of the type manufactured by Analog Devices as Part Number AD7115.

The cardiac signal is buffered by the voltage follower amplifier 84 to provide a relatively low driving point impedance to attenuator 86. The output of attenuator 86 is buffered through another voltage follower amplifier 88 which supplies an output through a series resistor 90 to a VVI (Ventricular Sense, Ventricular Pace, Inhibit) pacer 92 as shown. In this way, the impedance which the pacer sees will be almost exclusively the resistance of resistor 90.

The attenuator 86 can be a CMOS step-type attenuator which provides "N" steps of attenuation where "N" is a BCD number, for example, between 0 and 199. This results in each step being 0.1 dB, so that the range of attenuation is between 0 and 19.9 dB as indicated by 9 BCD control lines 94 supplied to a 9-bit latch 96 associated with the attenuator. For manual applications, the BCD input lines 94 can be controlled via three thumbwheel selectors, or other type of switches (not shown). However, for fully automated applications, the BCD lines 94 are under microprocessor control by latch 96.

From zero to small values of attenuation, the pacer sense amplifier of pacer 92 causes the output pulses therefrom to be inhibited, i.e., to provide no pace indicator action. When the sense margin threshold is reached, the pacer 92 outputs pacing pulses at its programmed rate. These (negative voltge) pulses cause a detector/comparator 98 to change its output on line 99 to a logic high level, triggering a monostable multivibrator or one shot circuit 100. This sends a drive signal to the pace indicator 72, which may typically be one or more light emitting diodes (LED's). The one shot circuit 100 insures that the pace indicator 72 is energized long enough to be unmistakably viewed by the user or detected by a microprocessor.

Figure 5:
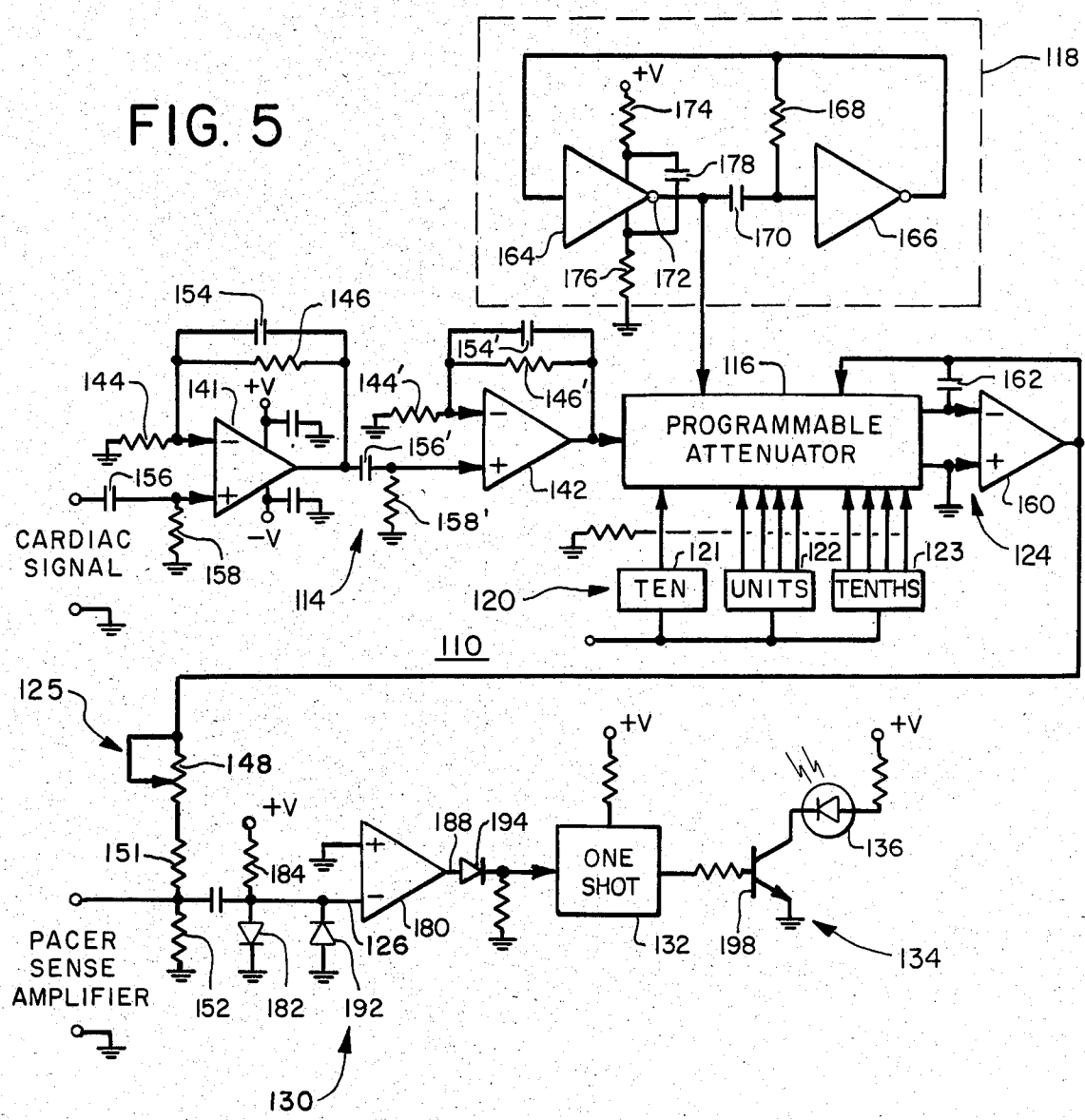
FIG. 5 is a schematic circuit diagram of the sense margin evaluation system of FIG. 4.
Figure 6:
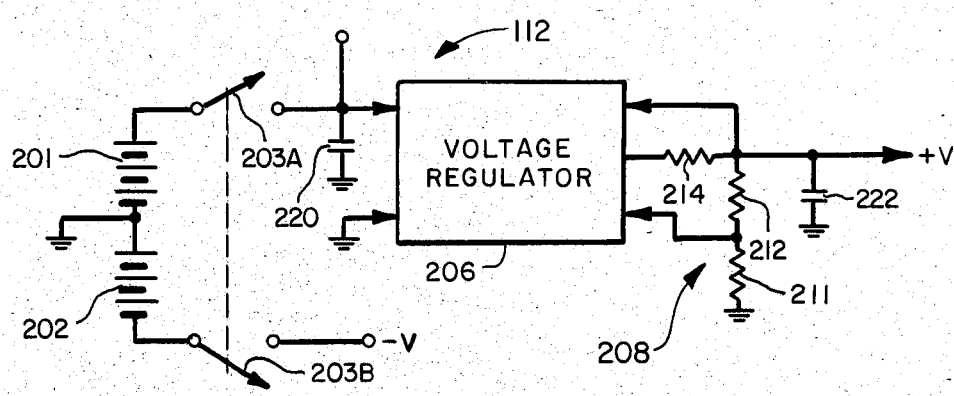
FIG. 6 is a schematic circuit diagram of a power supply for use with the sense margin evaluation system of FIG. 5.

A more detailed embodiment of the sense margin evaluation system of the present invention is generally identified by the reference number 110 in FIG. 5. The system 110 is powered by a conventional regulated dual-voltage supply 112 as shown in FIG. 6.

Basically, the sense margin evaluation system 110 comprises a two-stage bandpass amplifier circuit 114, a wide-band programmable attenuator 116, which is clocked by an oscillator 118 and which has coupled thereto programmable control switches 120 including switches 121 for ten, 122 for units and 123 for tenths (maximum 19.9 dB). The output of the programmable attenuator 116 is coupled through an amplifier buffer circuit 124 and a fixed attenuator network 125 to a VVI pacer. The buffered signal on an output line 126 is connected to the input of a detector circuit 130. The output of the detector circuit 130 is supplied to a one shot 132 which has an output coupled to a pace indicating circuit 134 which includes a light emitting diode 136.

Due to the low level nature of the endocardial signals supplied to the evaluation system, the bandpass amplifier circuit 114 is provided and utilized to maintain a good signal-to-noise ratio. This circuit comprises two operational amplifiers 141 and 142.

Operational amplifier 141 forms part of a first stage of amplifier 114 and has a mid-band gain of 10 as determined by resistors 144 and 146. Operational amplifier 142 forms part of a second stage and is identical to the first stage, thus establishing a net gain at 100. For input signals between ±0.5 mV to ±25 mV, the input to the programmable attenuator 116 will range from ±50 mV to ±2.5 volts. The overall system gain is adjusted for unity by a variable resistor 148 which, in conjunction with resistors 151 and 152, comprises the fixed attenuator 125. This adjustment is made during manufacture with the programmable attenuator set to zero dB using a mid-band 100 Hz sine wave.

In one embodiment of the present invention, the filter circuitry comprising resistors 146/146', capacitors 154/154' and 156/156' and resistors 158/158' pass a broad band of frequencies from 0.1 to 310 Hz. Capacitor 156 and resistor 158 add a first order high pass filter with a −3 dB cutoff frequency (FL) of approximately 0.08 Hz. Since the second stage including operational amplifier 142 is identical to the first stage, the net lower 3 dB frequency may be approximated by $F'_L = F_L \sqrt{2}$ or 0.11 Hz. Likewise the net upper 3 dB frequency may be approximately by $F'_H/\sqrt{2}$ or 310 Hz. The "roll off" is 40 dB/decade as expected for a two pole R-C filter.

The programmable attenuator 116 can be realized by a type AD7115 attenuator or similar attenuating device and will attenuate the input from 0 to 19.9 dB in 0.1 dB increments. The degree of attenuation is determined by a BCD input code which is latched in a write operation.

An operational amplifier 160 buffers the output of attenuator 116. An external feedback capacitor 162 compensates for phase lag of the attenuator without affecting the overall band width.

The oscillator 118, which includes two CMOS logic inverters 164 and 166, a resistor 168, and a capacitor 170, generates a square wave logic signal at an output pin 172. The period of oscillation is determined by $T = 1.6 \times$ (value of resistor 168) $\times$ (value of capacitor 170) $\pm 10\%$, and in one embodiment of this invention is approximately 50 Hz.

Since oscillator 118 and attenuator 116 share the same power supply, extra care in decoupling is essential in reducing interference. This is achieved by providing a resistor 174 having a relatively high resistance, such as, for example, 10K ohms, in each of the supply leads together with a capacitor 178 having a relatively high capacitance, for example, 0.1 μf. This results in a noise reduction on the +V line from 20 mVpp to 8 mVpp (max). It will be understood, of course, that proper decoupling, component layout, shielding and grounding are essential for noise-free operation.

The detector circuit 130 includes a comparator amplifier 180 for detecting pacer output pulses at the threshold of sensing. At a quiescent mode of operation, a diode 182 is forward biased through resistor 184, applying positive voltage to the inverting input 126 of comparator 180. As a result, the output of the comparator at 188 is quiescently at negative saturation (−9V). A diode 194 is back biased to protect the one shot circuit 132 from negative voltage.

As the attenuation is increased, the cardiac signal falls below the pacer sense amplifier's sensing threshold. The pacer then outputs a negative pulse which causes diode 192 to become forward-biased. This transition triggers the one shot circuit 132 to apply a 100 millisecond positive pulse to the base of transistor 198 in pace indicating circuit 134, turning transistor 198 on. When transistor 198 is on, LED 136 is energized to emit light.

Referring to FIG. 6, the system power supply 112 may be supplied by two 9 volt alkaline batteries 201 and 202. This voltage is applied through a DPST ON/OFF switch 203A and 203B to a voltage regulator circuit 206 having a voltage divider network 208 comprising resistors 211 and 212 connected thereto. This divider circuit 208 is used to scale the reference voltage ($V_{set} = 1.3$ V) using the formula:

$$V_{out} = 1 + \left[ \frac{\text{(value of resistor 211)}}{\text{(value of resistor 212)}} \right] \times V_{set}$$

Current is limited by a series-connected resistor 214 at 0.7/value of the resistor. In the event that the current drain exceeds 11 milliamps, a comparator shuts down the evaluation system 110, protecting both the voltage regulator 206 and the circuits 114, 116, 118, 130, 132 and 134 it powers. A capacitor 220 is connected across the input of voltage regulator 206 to limit potentially harmful transients, and a capacitor 222 is connected across the output of voltage regulator 206 to improve rejection of AC fluctuations.

From the foregoing description it will be apparent that the sense margin evaluation system of the present invention provides the advantage of meaningful matching of the sensitivity of a pacer with the amplitude of a patient's cardiac signal. Also, the system is highly reliable, and with the broad-band bandpass amplifier circuitry shown, prevents reading errors and/or problems due to mismatch between a patient's heart and the sense amplifier of an implantable pacer.

While particular embodiments of the invention have been shown and described, it will be understood that changes and modifications may be made therein without departing from the teachings of the invention. Accordingly, the scope of the invention is only to be limited as necessitated by the accompanying claims.

We claim:

1. An apparatus for enabling an in-vivo determination of the ratio or "sense margin" between the effective amplitude of a cardiac signal (R-wave or P-wave) from a patient's heart and the minimum attenuated amplitude of said signal which can be readily sensed by a sense amplifier in a pacer to be implanted in the patient's heart where:

$$\text{Sense Margin} = \text{Maximum allowable signal attenuation} = \frac{\text{Effective cardiac amplitude}}{\text{Effective pacer sense amplifier threshold}}$$

said apparatus comprising:
a bandpass adjustable attenuator circuit having an input and an output, said bandpass being greater than the bandpass of the sense amplifier and the frequency spectrum of the cardiac signal;
first means for coupling said attenuator circuit input to at least one cardiac signal sensing probe connected to the patient's heart;
second means for coupling said attenuator circuit output to the sense amplifier in the pacer;
means coupled to the pacer for detecting a pacing pulse generated by the pacer;
means coupled to said attenuator circuit for controlling cardiac signal attenuation and for ascertaining the amount of attenuation at the time a pacing pulse is detected to enable a numerical determination of the sense margin ratio to be made by expression of the maximum attenuation value as a ratio of: signal input/signal output.

2. The apparatus of claim 1 wherein said first input coupling means comprise an amplifier with a broader bandpass than the spectrum of the signals of interest to enhance the signal-to-noise ratio while continuing to provide a net passband which is considerably greater than that of the sense amplifier so that operation of said apparatus is independent of the passbands of the sense amplifier and the frequency spectrum of the cardiac signal.

3. The apparatus of claim 1 wherein said attenuator circuit includes a programmable attentuator and an oscillator circuit coupled to said programmable attenuator.

4. The apparatus of claim 1 including a regulated power supply circuit for providing regulated voltage to said attenuator circuit and associated circuits.

5. The apparatus of claim 1 wherein said means for detecting a pacer pulse includes a visual display device for providing a visual indication of when a pulse is detected.

6. The apparatus of claim 5 wherein said visual display device is a light emitting diode.

7. The apparatus of claim 1 wherein said means for detecting a pacer pulse includes non-visual means for generating a "pulse detected" signal.

8. The apparatus of claim 1 wherein said means for detecting a pacing pulse includes a comparator having one input coupled to a pacer output, a threshold reference voltage coupled to the other input of said comparator and a univibrator (one shot) coupled to the output of said comparator for providing a pulse detected signal.

9. The apparatus of claim 8 wherein said means for detecting a pacing pulse further includes a light emitting diode coupled to the output of said univibrator for providing a visual indication of "pulse detected".

10. The apparatus of claim 1 wherein said attenuator circuit includes manually controlled means including an encoded set of switches for adjusting the attenuation and including means for displaying the signal attenuation in decibels.

11. The apparatus of claim 1 wherein said attenuator circuit includes a digitally controlled, incremental step-type attenuator circuit.

12. The apparatus of claim 1 wherein said means for controlling attenuation and for ascertaining when a pacer pulse is detected includes a microprocessor coupled to said attenuator circuit for providing automatic control of the attenuation.

13. The apparatus of claim 12 including a digital-to-analog converter coupled between said microprocessor and said attenuator circuit for controlling signal attenuation.

14. The apparatus of claim 1 including an analog signal divider coupled to said attenuator circuit for adjusting the attenuation.

15. The apparatus of claim 1 wherein said bandpass adjustable attenuator circuit has a bandpass between 10 and 200 Hz.

16. The apparatus of claim 1 wherein said bypass adjustable attenuator circuit has a bandpass between 0.1 and 480 Hz.

17. The apparatus of claim 1 including a microprocessor and means coupled to said means for detecting a pacing pulse for routing a "pulse detected" signal to said microprocessor.

18. The apparatus of claim 1 wherein said first coupling means includes buffer circuit means so that the operation of said apparatus is substantially independent of the pacing lead's output impedance.

19. The apparatus of claim 1 wherein said second coupling means includes buffer circuit means so that the operation of said apparatus is substantially independent of the pacer sense amplifier's input impedance.

20. The apparatus of claim 1 wherein said first coupling means includes buffer circuit means and said second coupling means includes buffer circuit means whereby opration of said apparatus is substantially independent of the pacing lead's output impedance and the pacer sense amplifier's input impedance.

21. A method for determining in-vivo the ratio or "sense margin" between the effective amplitude of a cardiac signal (R-wave or P-wave) from a patient's heart and the mininum attenuated amplitude of said signal which can be readily sensed by a sense amplifier in a pacer to be implanted in the patient where:

$$\text{Sense Margin} = \frac{\text{Effective cardiac amplitude}}{\text{Effective pacer sense amplifier threshold}}$$

said method comprising the steps of:
coupling a sensing/pacing electrode to the patient's heart;

coupling a lead from the sensing/pacing electrode to the input of a sense margin determining apparatus including a bandpass attenuator circuit, said bandpass being greater than the bandpass of the sense amplifier and the frequency spectrum of the cardiac signal;

coupling the output from said bandpass attenuator circuit to a pacer sense amplifier in a pacer;

coupling a pacing pulse detecting circut to the output of the pacer;

setting the attenuator circuit to zero attenuation;

placing the pacer in a standby/sense mode of operation;

attenuating the cardiac signals received in an iterative process, continuously or in steps;

simultaneously monitoring the output of the pulse detecting circuit to see if a pacer pulse has been detected;

detecting when a pacer pulse is generated by the pacer and noting the amount of attenuation of the attenuated signal received by the pacer sense amplifier when an pacer pulse is generated;

converting the attenuated value of effective cardiac signal when a pulse is generated, relative to the value of the cardiac signal sensed to a ratio; and determining if the ratio or sense margin is at least 1.1:1 (effective cardiac signal value to attenuated cardiac signal value which is below the sense amplifier threshold such that a pacer pulse is generated by the pacer), and if so, proceeding with the inplanting of the pacer, and if not, taking corrective action such as: checking the electrode connection to the heart and the pacer circuitry and/or adjusting the gain of the sense amplifier, or repeating the above steps with a new electrode coupled to the heart and/or a new pacer.

22. The method of claim 21 including the step of monitoring a visual display device included in said pulse circuit whereby pulse detection is visually monitored.

23. The method of claim 21 wherein the step of monitoring the pulse detecting circuit comprises visually monitoring a visual display of detected pulses.

24. The method of claim 21 wherein the cardiac input signal is attenuated in an analog manner, i.e., continuously, as opposed to incrementally.

25. The method of claimed 21 wherein the cardiac input signal is attenuated in increments of 0.1 dB.

26. The method of claim 21 wherein said step of determining if the ratio or sense margin is above 1.1:1 includes determining if the ratio or sense margin is above 2:1.

27. The method of claim 21 including the additional steps of:
amplifying the incoming cardiac signal a set amount to obtain a higher signal-to-noise ratio;
and attenuating the output signal from the attenuator circuit by said set amount prior to supplying same to the pacer sense amplifer.

28. The method of claim 21 including the step of electronically buffering the coupling of the pacing lead to the input of the sense margin determining apparatus so that said determination is substantially independent of the pacing lead output impedance.

29. The method of claim 21 including the step of electronically buffering the coupling to the input to the pacer sense amplifier so that said determination is substantially independent of the pacer sense amplifier's input impedance.

30. The method of claim 21 including the steps of electronically buffereing the coupling of the pacing lead to the input of the sense margin determining apparatus so that said determination is substantially independent of the pacing lead output impedance; and electronically buffering the coupling to the input to the pacer sense amplifier so that said determination is substantially independent of the pacer sense amplifier's input impedance.

31. A system for enabling an in-vivo determination of the ratio or "sense margin" between the effective amplitude of a living body generated signal sensed by a sensing probe in a living body and the minimum attenuated amplitude of said signal which can be readily sensed by a sense amplifier in a stimulator to be implanted in the living body where:

Sense Margin = Maximum allowable signal attenuation $$= \frac{\text{Effective signal amplitude}}{\text{Effective sense amplifier threshold}}$$

said system comprising:
a bandpass adjustable attenuator circuit having an input and an output, said bandpass being greater than the bandpass of the sense amplifier and the frequency spectrum of the living body generated signal;

first means for coupling said attenuator circuit input to a signal sensing probe;

second means for coupling said attenuator circuit output to the sense amplifier;

means coupled to the stimulator for detecting a stimulation signal generated by the stimulator when the sense amplifier cannot sense the attenuated living body generated signal;

means coupled to said attenuator circuit for controlling the attenuation of the living body generated signal and for ascertaining the amount of attenuation when a stimulation signal is detected to enable a numerical determination of the sense margin ratio to be made by expression of the maximum attenuation value at which a stimulation signal is generated by the stimulator as a ratio of: living body generated signal input/stimulator generated signal output.

32. A system for enabling an in-vivo determination of the ratio or "sense margin" between the effective amplitude of a living body generated signal sensed by a sensing probe in a living body and the minimum attenuated amplitude of said signal which can be readily sensed by a sense amplifier in a stimulator to be implanted in a living body where:

Sense Margin = Maximum allowable signal attenuation $$= \frac{\text{Effective signal amplitude}}{\text{Effective sense amplifier threshold}}$$

said system comprising:
an adjustable attenuator circuit having an input and an output;

first means for coupling said attenuator circuit input to a signal sensing probe, said first coupling means including buffer circuit means so that operation of said system is substantially independent of the sensing probe's output impedance;

second means for coupling said attenuator circuit output to the sense amplifier; said second coupling means including buffer circuit means so that operation of said system is substantially independent of the sense amplifier's input impedance;

means coupled to the stimulator for detecting a stimulation signal generated by the stimulator when the sense amplifier cannot sense the attenuated living body generated signal;

means coupled to said attenuator circuit for controlling the attenuation of the living body generated signal and for ascertaining the amount of attenuation when a stimulation signal is detected to enable a numerical determination of the maximum attenuation value at which a stimulation signal is generated by the stimulator as a ratio of: living body generated signal input/stimulator generated signal output.

33. A system for enabling an in-vivo determination of the ratio or "sense margin" between the effective amplitude of a lving body generated signal sensed by a sensing probe in a living body and the minimum attenuated amplitude of said signal which can be readily sensed by a sense amplifier in a stimulator to be implanted in the living body where:

Sense Margin = Maximum allowable signal attenuation $$= \frac{\text{Effective signal amplitude}}{\text{Effective sense amplifier threshold}}$$

said system comprising:

a bandpass adjustable attenuator circuit having an input and an output, said bandpass being greater than the bandpass of the sense amplifier and the frequency spectrum of the living body generated signal;

first means for coupling said attenuator circuit input to a signal sensing probe, said first coupling means including buffer circuit means so that operation of said system is substantially independent of the sensing probe's output impedance;

second means for coupling said attenuator circuit output to the sense amplifier, said second coupling means including buffer circuit means so that operation of said system is substantially independent of the sense amplifier's input impedance;

means coupled to the stimulator detecting a stimulation signal generated by the stimulator when the sense amplifier cannot sense the attenuated living body generated signal;

means coupled to said attenuator circuit for controlling the attenuation of the living body generated signal and for ascertaining the amount of attenuation when a stimulation signal is detected to enable a numerical determination of the sense margin ratio to be made by expression of the maximum attenuation value at which a stimulation signal is generated by the stimulator as a ratio of: living body generated signal input/stimulator generated signal output.

34. A method for determining in-vivo the ratio or "sense margin" between the effective amplitude of a living body generated signal sensed by a sensing probe in a living body and the minimum attenuated amplitude of said signal which can be readily sensed by a sense margin amplifier in a stimulator to be implanted in the living body where:

Sense Margin = Maximum allowable signal attenuation $$= \frac{\text{Effective signal amplitude}}{\text{Effective sense amplifier threshold}}$$

said method compring the steps of:

coupling a sensing probe to a living body;

coupling a lead from the sensing probe to the input of a sense margin determining apparatus including a bandpass adjustable attenuating circuit having an input and an output, said bandpass being greater than the bandpass of the sense amplifier and the frequency spectrum of the living body generated signal;

coupling the output from said attenuator circuit to the sense amplifier;

coupling a detector for detecting a stimulation signal to the output of the stimulator;

attenuating the living body generated signal in an iterative process, continuously or in steps;

simultaneously monitoring the output of the stimulator to see if a stimulation signal has been generated;

detecting when a stimulation signal is generated by the stimulator;

noting the amount of attenuation of the attenuated signal received by the sense amplifier when a stimulation signal is generated; and expressing the maximum attenuation value at which a stimulation signal is generated by the stimular as a ratio of: living body generated signal input/stimulator generated signal output.

35. A method for determining in-vivo the ratio or "sense margin" between the effective amplitude of a living body generated signal sensed by a sensing probe in a living body and the minimum attenuated amplitude of said signal which can be readily sensed by a sense amplifier and a stimulator to be implanted in the living body, where:

Sense Margin = Maximum allowable signal attenuation $$= \frac{\text{Effective signal amplitude}}{\text{Effective sense amplifier threshold}}$$

said method comprising the steps of:

coupling a sensing probe to a living body;

coupling a lead from the sensing probe to the input of a sense margin determining apparatus including an adjustable attenuator circuit having an input and an output;

electronically buffering the coupling of the lead to the input of the sense margin determining apparatus so that said determination is substantially independent of the lead output impedance;

coupling the output from said attenuator circuit to the sense amplifier;

electronically buffering the coupling to the input signal to the sense amplifier so that said determination is substantially independent of the sense amplifier's input impedance;

coupling a detector for detecting a stimulation signal to the output of the stimulator;

attenuating the living body generated signal in an iterative process, continuously or in steps;

simultaneously monitoring the output of the stimulator to see if the stimulation signal has been generated;

detecting when a stimulation signal is generated by the stimulator;

noting the amount of attenuation of the attenuated signal received by the sense amplifier when a stimulation signal is generated; and, expressing the maximum value at which a stimulation signal is generated by the stimulator as a ratio of: living body generated signal input/stimulator generated signal output.

36. A method for determining in-vivo the ratio or "sense margin" between the effective amplitude of a living body generated signal sensed by a sensing probe in a living body and the minmum attenuated amplitude of said signal which can be readily sensed by a sense amplifier and a stimulator to be implanted in the living body, where:

$$\text{Sense Margin} = \text{Maximum allowable signal attenuation} = \frac{\text{Effective signal amplitude}}{\text{Effective sense amplifier threshold}}$$

said method comprising the steps of:

coupling a sensing probe to a living body;

coupling a lead from the sensing probe to the input of a sense margin determining apparatus including a band passage adjustable attenuating circuit having an input and an output, said bandpass being greater than the bandpass of the sense amplifier and the frequency spectrum of the living body generated signal;

electronically buffering the coupling of the lead to the input of the sense margin determining apparatus so that said determination is substantially independent of the lead output impedance;

coupling the output from said attenuator circuit to the sense amplifier;

electronically buffering the coupling to the input signal to the sense amplifier so that said determination is substantially independent of the sense amplifier's input impedance;

coupling a detector for detecting a stimulation signal to the output of the stimulator;

attenuating the living body generated signal in an iterative process, continuously or in steps;

simultaneously monitoring the output of the stimulator to see if the stimulation signal has been generated;

detecting when a stimulation signal is generated by the stimulator;

noting the amount of attenuation of the attenuated signal received by the sense amplifier when a stimulation signal is generated; and, expressing the maximum attenuation value at which a stimulation signal is generated by the stimulator as a ratio of: living body generated signal input/stimulator generated signal output.

* * * * *

UNITED STATES PATENT AND TRADEMARK OFFICE
CERTIFICATE OF CORRECTION

PATENT NO. : 4,640,285         Page 1 of 3

DATED : February 3, 1987

INVENTOR(S) : DeCote, Jr. et al.

It is certified that error appears in the above-identified patent and that said Letters Patent is hereby corrected as shown below:

Title 54 "USE" should be --USING--.

Abstract 57 , line 22, "amplifier'" should be --amplifier's--.

Column 1, line 2, "USE" should be --USING--.

Column 4, line 38, "amplifer" should be --amplifier--.

Column 7, line 31, "physican" should be --physician--.

Column 8, line 30, "sensivity" should be --sensitivity--.

Column 9, line 6, "voltge" should be --voltage--.

Column 13, line 9, "circut" should be --circuit--;

line 22, "an" should be --a--;

line 31, "inplanting" should be --implanting--;

line 39, before the word "circuit" insert --detecting--;

UNITED STATES PATENT AND TRADEMARK OFFICE
CERTIFICATE OF CORRECTION

PATENT NO. : 4,640,285  Page 2 of 3
DATED : February 3, 1987
INVENTOR(S) : DeCote, Jr. et al.

It is certified that error appears in the above-identified patent and that said Letters Patent is hereby corrected as shown below:

line 46, "claimed" should be --claim--.

Column 14, line 2, "buffereing" should be --buffering--;

line 62, ";" should be --:--.

Column 15, line 19, "lving" should be --living--;

line 46, insert before the word "detecting" --for--;

line 66, beforethe word "where" insert --,--.

Column 16, line 6, "compring" should be --comprising--;

line 13, "spetrum" should be --spectrum--;

line 27, after the word "and" insert --,--;

line 30, "stimular" should be --stimulator--.

Column 17, line 6, before the word "value" insert --attenuation--.

UNITED STATES PATENT AND TRADEMARK OFFICE
CERTIFICATE OF CORRECTION

PATENT NO. : 4,640,285  Page 3 of 3

DATED : February 3, 1987

INVENTOR(S) : DeCote, Jr. et al.

It is certified that error appears in the above-identified patent and that said Letters Patent is hereby corrected as shown below:

line 13, "minmum" should be --minimum--.

Signed and Sealed this

Twenty-fifth Day of August, 1987

*Attest:*

DONALD J. QUIGG

*Attesting Officer*    Commissioner of Patents and Trademarks